(12) United States Patent
Asada

(10) Patent No.: US 11,433,229 B2
(45) Date of Patent: Sep. 6, 2022

(54) TWO-WAY PRESSURE RELIEF VALVE FOR RESERVOIR

(71) Applicant: TERUMO CARDIOVASCULAR SYSTEMS CORPORATION, Ann Arbor, MI (US)

(72) Inventor: Takehiko Asada, Bear, DE (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 323 days.

(21) Appl. No.: 16/891,173

(22) Filed: Jun. 3, 2020

(65) Prior Publication Data
US 2021/0379351 A1 Dec. 9, 2021

(51) Int. Cl.
*A61M 39/24* (2006.01)
*A61M 39/22* (2006.01)
*A61M 39/26* (2006.01)

(52) U.S. Cl.
CPC .......... *A61M 39/24* (2013.01); *A61M 39/228* (2013.01); *A61M 39/26* (2013.01); *A61M 2039/248* (2013.01); *A61M 2039/2413* (2013.01); *A61M 2039/267* (2013.01)

(58) Field of Classification Search
CPC .... A61M 39/24; A61M 39/228; A61M 39/26; A61M 2039/2413; A61M 2039/248; A61M 2039/267
See application file for complete search history.

(56) References Cited

U.S. PATENT DOCUMENTS

| 4,317,467 A | * | 3/1982 | Heyland | .......... B60K 15/03519 |
| | | | | 137/538 |
| RE31,121 E | * | 1/1983 | Reinicke | ................. A61F 2/004 |
| | | | | 137/493 |
| 4,561,559 A | * | 12/1985 | Rutan | ................... F16K 17/196 |
| | | | | 220/203.26 |
| 4,781,686 A | | 11/1988 | Erickson | |
| 6,017,493 A | | 1/2000 | Cambron et al. | |
| 6,217,635 B1 | * | 4/2001 | Conrad | ............... B01D 53/053 |
| | | | | 96/144 |

(Continued)

FOREIGN PATENT DOCUMENTS

EP 0617627 B1 5/1996
EP 0766974 A2 9/1997

*Primary Examiner* — Patrick C Williams
(74) *Attorney, Agent, or Firm* — Darryl Newell; MacMillan, Sobanski & Todd, LLC

(57) ABSTRACT

A pressure relief valve for a reservoir has a main body with a central chamber defining an outer radial seat, a positive-pressure port with an inner radial seat, and a negative-pressure port comprising an internal passage spanning the outer seat. The sealing disk has an anchor body retained in the central chamber and a flexible diaphragm biased against the outer seat. An axial passage in the anchor body couples the central chamber to ambient atmospheric pressure. The sealing ball is biased against the inner seat. When a pressure inside the reservoir exceeds ambient by a positive-pressure threshold, then the sealing ball lifts off the inner radial seat to exhaust a gas through the positive-pressure port. When the pressure inside the reservoir is below ambient by a negative-pressure threshold, then the diaphragm is lifted off the outer seat to intake atmospheric gas into the reservoir.

20 Claims, 7 Drawing Sheets

(56) References Cited

U.S. PATENT DOCUMENTS 6,726,059 B2 * 4/2004 Treat .................... F16K 15/142
                                                               137/493.1
9,435,450 B2    9/2016 Muennich
11,191,943 B1 * 12/2021 Asada .................. F16K 17/194

* cited by examiner

TWO-WAY PRESSURE RELIEF VALVE FOR RESERVOIR

CROSS REFERENCE TO RELATED APPLICATIONS

Not Applicable.

STATEMENT REGARDING FEDERALLY SPONSORED RESEARCH

Not Applicable.

BACKGROUND OF THE INVENTION

The present invention relates in general to medical fluid reservoirs such as a blood reservoir of a perfusion system, and, more specifically, to a pressure relief valve for a medical fluid reservoir.

Fluid systems commonly include components such as tubing, pumps, reservoirs, heat exchangers, sensors, filters, valves, and the like. Such components can be connected together in a network to define a fluid flow path. Some fluid systems are open systems, meaning that the fluid flows through the network once and then exits the network. Other fluid systems are closed systems, meaning that the fluid recirculates within the network of components. Fluids are caused to flow in the fluid system using fluid pressure differentials. In some cases, a pump is used to create a pressure differential that causes the fluid to flow within the fluid system. In other cases, a vacuum source, gravity, or a combination of such techniques can be used to create a pressure differential that causes the fluid to flow within the fluid system.

Reservoirs can be used as components of fluid systems for various purposes. In some cases, reservoirs are used for accumulation or storage of the fluid. The storage of a fluid in a reservoir can facilitate a steady outgoing flow of the fluid, despite having an unsteady incoming flow of the fluid. Reservoirs can also be used to facilitate control of the pressure of the fluid within the fluid system. Some reservoirs are completely filled with the fluid, while other reservoirs include an airspace above the level of the fluid in the reservoir.

In the case of a closed reservoir which is not open to ambient atmospheric pressure, the pressure within a reservoir may be higher or lower than the ambient air pressure on the outside of the reservoir. Such pressure differentials can be advantageous when the extent of the pressure differential is within the design parameters of the fluid system. However, in some circumstances the pressure differential between the ambient air and the interior of a reservoir can become greater than intended, and undesirable consequences can result. Such undesirable consequences may include deviating from being in a state of control of the fluid flow, excessive pressure or vacuum levels within the fluid system, damage to the reservoir or another fluid system component, and the like.

Fluid systems are often used in a medical context. Some examples of fluid systems used in the medical context include respiratory systems, anesthesia systems, infusion pump systems, blood transfusion circuits, kidney dialysis systems, extracorporeal membrane oxygenation (ECMO) systems, extracorporeal circuits for heart/lung bypass, and the like. Some such medical fluid systems include the use of medical fluid reservoirs.

As with other types of fluid reservoirs, medical fluid reservoirs may experience a pressure differential between the ambient air and the interior of the medical fluid reservoir that is greater than intended. In some cases, excessive differential pressures can result in undesirable consequences that may damage the medical fluid system or could hamper the desired fluid flow. To avoid such undesirable pressure differentials, one or more pressure relief valves have been used in fluid communication with a reservoir. One such relief valve is disclosed in U.S. Pat. No. 9,435,450, entitled "Pressure Differential Relief Valve," which is incorporated herein by reference in its entirety.

In the medical context, devices that come in contact with blood or other patient fluids must meet special requirements such as biocompatibility and sterility, for example. A single unit providing relief for both excessive negative pressure and excessive positive pressure is very desirable. High reliability for performing pressure relief is necessary, and a compact design would be beneficial for incorporating a valve into a reservoir in a convenient location while avoiding any need to increase the size of the reservoir. In addition, a low cost is highly desirable in order to enable disposability of devices (which further increases patient safety). These potentially conflicting criteria have created an ongoing need for improvement in pressure relief valves.

SUMMARY OF THE INVENTION

In some embodiments, the invention provides two-way pressure relief in a single valve device which combines a ball valve and a diaphragm valve in a shared housing. The compact design achieves low material and manufacturing costs. The valve of the invention provides reliable, robust sealing and enables any desired thresholds for both negative and positive pressure to be easily obtained with simple variations of an overall design.

In one aspect of the invention, a differential pressure relief valve for a medical reservoir comprises a main body, a sealing disk, and a sealing ball. The main body is adapted to mount to a wall of the reservoir. The main body has a central chamber defining an outer radial seat, a positive-pressure port at a center axis with an inner radial seat, and a negative-pressure port comprising an internal passage spanning the outer radial seat. The sealing disk has an anchor body retained in the central chamber and a flexible diaphragm biased against the outer radial seat. The anchor body defines an axial passage coupling the central chamber to an ambient pressure of an atmosphere outside the reservoir. The sealing ball is biased against the inner radial seat. When a pressure inside the reservoir exceeds the ambient pressure by a positive-pressure threshold, then the sealing ball is lifted off the inner radial seat to exhaust a gas through the positive-pressure port and the axial passage to the atmosphere. When the pressure inside the reservoir is below the ambient pressure by a negative-pressure threshold, then the diaphragm is lifted off the outer radial seat to intake a gas from the atmosphere into the reservoir through the axial passage, the internal passage, and the negative-pressure port.

DETAILED DESCRIPTION OF PREFERRED EMBODIMENTS

Figure 1:
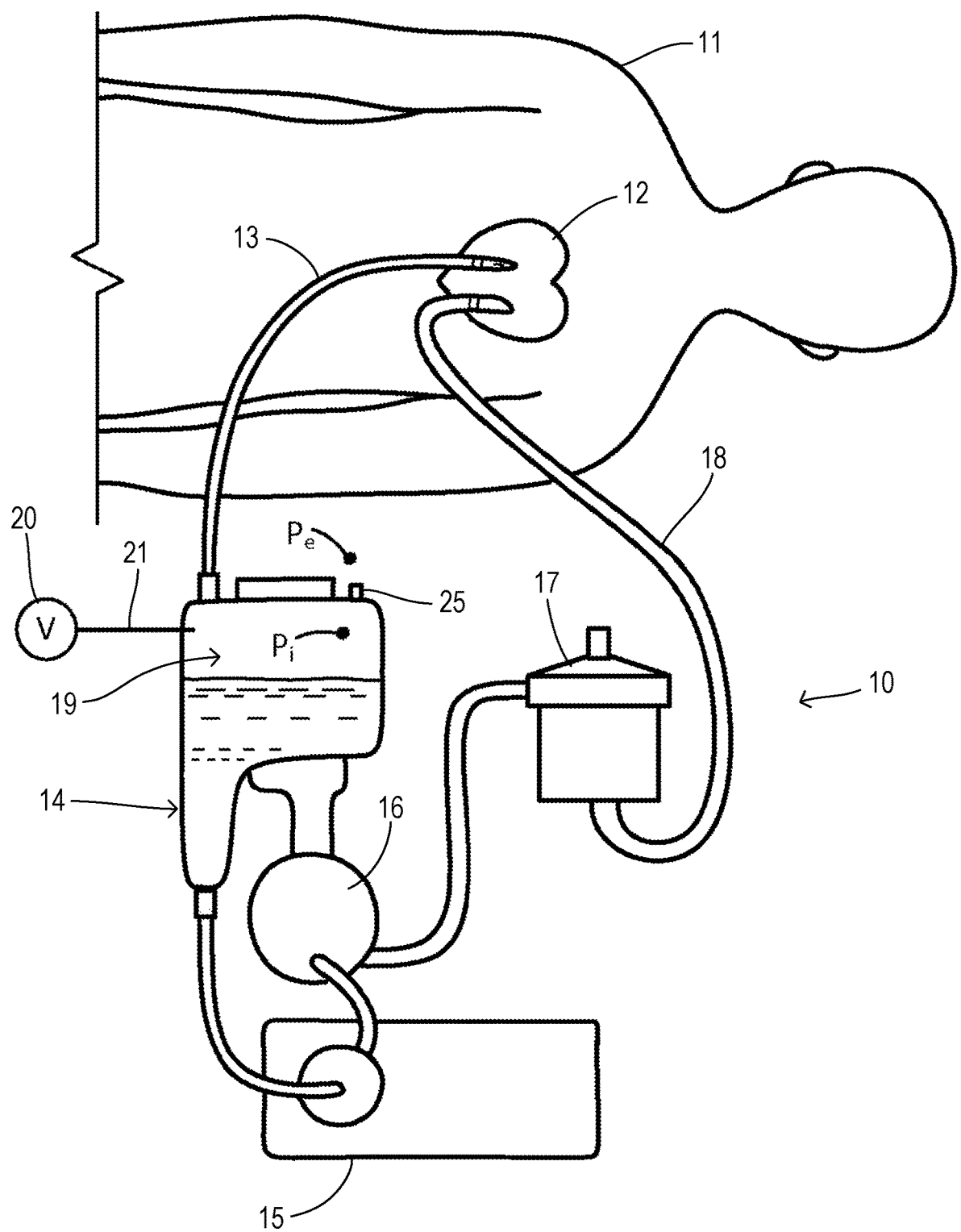
FIG. 1 is a schematic diagram of patient undergoing an example medical procedure using an extracorporeal blood flow circuit that includes a medical fluid reservoir.

Referring to FIG. 1, a patient 11 can receive a medical treatment while using a medical fluid system 10. In this illustrative example, patient 11 is undergoing a heart bypass procedure using an extracorporeal blood flow circuit 10 connected to patient 11 at the patient's heart 12. Blood from patient 11 is extracted at or near heart 12, the blood is circulated through circuit 10, and then the blood is returned to the patient's heart 12.

Extracorporeal blood flow circuit 10 includes, at least, a venous tube 13, a blood reservoir 14, a pump 15, an oxygenator 16, an arterial filter 17, and an arterial tube 18. Venous tube 13 is in physical contact with heart 12 and in fluid communication with the venous side of the circulatory system of patient 11. Venous tube 13 is also in fluid communication with an inlet to reservoir 14. An outlet from reservoir 14 is connected by tubing to an inlet of pump 15. The outlet of pump 15 is connected to tubing to an inlet of oxygenator 16. The outlet of oxygenator 16 is connected by tubing to an inlet of arterial filter 17. An outlet of arterial filter 17 is connected to arterial tube 18. Arterial tube 18 is in physical contact with heart 12 and in fluid communication with the arterial side of the circulatory system of patient 11.

Briefly, extracorporeal blood flow circuit 10 operates by removing venous blood from patient 11 via venous tube 13. Blood from venous tube 13 is deposited in reservoir 14. At least some amount of blood is intended to be maintained in reservoir 14 at all times during the medical procedure. Blood from reservoir 14 is drawn from reservoir 14 by pump 15. The pressure generated by pump 15 propels the blood through oxygenator 16. In oxygenator 16 the venous blood is enriched with oxygen. The oxygen-rich arterial blood exits oxygenator 16, travels through arterial filter 17, and is injected into the patient's heart 12 by arterial tube 18.

The flow of blood through the extracorporeal blood flow circuit 10 is essentially continuous while the medical procedure is taking place. Within that overall context, an accumulation of blood exists in reservoir 14 during the procedure. The accumulation of blood within reservoir 14 serves multiple purposes. In one aspect, the accumulation of blood in reservoir 14 provides a buffer amount to help ensure a continuous flow of oxygenated blood to patient 11, even in the event that blood flow to reservoir 14 is interrupted. In another aspect, reservoir 14 allows the venous blood to deaerate. The deaeration of the venous blood takes place by allowing air bubbles in the blood to escape the blood and flow into the air. For at least that reason, an airspace 19 is maintained in reservoir 14.

As described above, the venous blood flows (drains) from heart 12 to reservoir 14. In some implementations, the venous blood drainage from heart 12 to reservoir 14 occurs primarily as a result of gravity. In such gravity drainage implementations, reservoir 14 is positioned at a lower elevation than heart 12. In result, the blood naturally flows 'downhill' from heart 12 to reservoir 14. In some implementations, a vacuum is drawn in the airspace 19 of reservoir 14 to assist with the drainage from heart 12 to reservoir 14. This technique is known as vacuum assisted venous drainage (VAVD).

During VAVD procedures, the venous drainage is assisted by placing reservoir 14 under a negative pressure (vacuum) in relation to the ambient pressure. For example, in some implementations a negative pressure is achieved within airspace 19 using a vacuum source 20 that is connected to reservoir 14 via a vacuum line 21. Vacuum source 20 is used to reduce an air pressure $P_i$ that is in interior airspace 19 of reservoir 14 to less than an air pressure $P_e$ at an ambient location that is externally adjacent to reservoir 14 (i.e., at atmospheric ambient pressure). To maintain an effective level of vacuum in airspace 19 when using VAVD, reservoir 14 is sealed in an essentially airtight manner. Consequently, an air pressure differential may exist between $P_i$ and $P_e$. Under normal operating conditions, the pressure differential between $P_i$ and $P_e$ (e.g., where $P_i<P_e$) is beneficial for assisting with the drainage of blood from heart 12 to reservoir 14.

In some scenarios, however, the pressure differential between $P_i$ and $P_e$ can become abnormal, and undesirable consequences can result. For example, in the event that vacuum line 21 becomes blocked or kinked, vacuum withdrawal of air from reservoir 14 might stop, and reservoir 14 (being sealed airtight) could build up a positive pressure at $P_i$ in relation to $P_e$. In that case, it is possible that pressurized air from airspace 19 can be forced from reservoir 14, through venous tube 13, and into heart 12 of patient 11. In another example, an excess of vacuum in reservoir 14 (too high of a pressure differential between $P_i$ and $P_e$) can result if there is a failure of a regulator of vacuum source 20, or if an incorrect set point is used for vacuum source 12. In such a case, the excess vacuum in airspace 19 of reservoir 14 can pull air across the membrane of oxygenator 16, causing air to be potentially sent to patient 11 via arterial tube 18. In some cases, excess negative pressure can also damage the blood cells. For these and other such reasons, the pressure differential between $P_i$ and $P_e$ can be beneficial when controlled within a desirable range of pressure, but can be detrimental when outside (above or below) the desirable range of pressure. Hence, a pressure differential relief device 25, that remedies both an excessive vacuum situation and an overpressure situation, can be advantageously used in conjunction with the reservoir 14. The benefits of such a pressure differential relief device can also be realized in the context of fluid circuits other than the example extracorporeal blood flow circuit 10, including in other medical applications.

Figure 2:
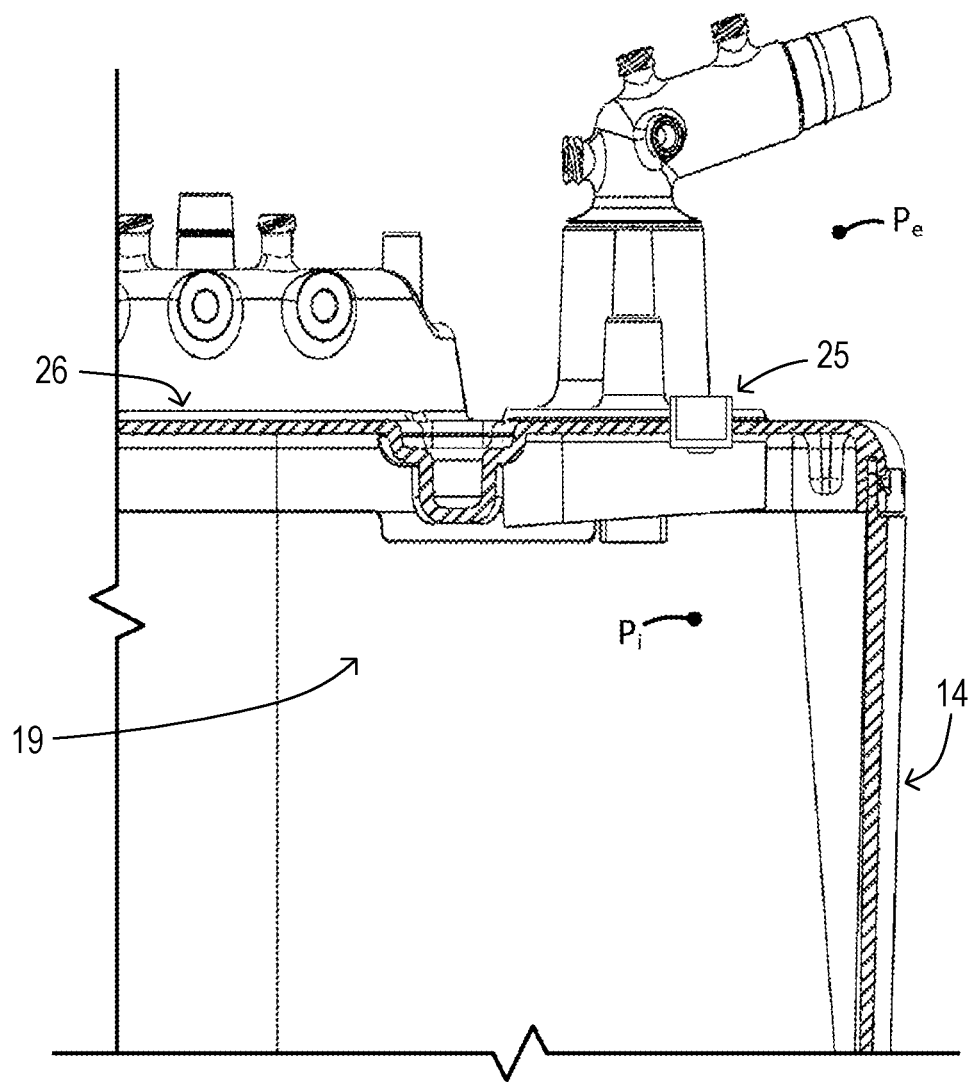
FIG. 2 is a partial cross-sectional view of an example medical fluid reservoir that includes a pressure differential relief valve in accordance with some embodiments provided herein.

As shown in FIG. 2, reservoir 14 can be formed as a plastic shell which includes a lid 26 for mounting pressure differential relief valve 25 to facilitate equalization of both positive and negative pressure differentials between $P_i$ and $P_e$. Lid 25 may also incorporate a connector for a venous tube. Valve 25 may be installed in an aperture through lid 26 so that one side of valve 25 is exposed to interior airspace 19 inside of the reservoir shell and the other side of valve 25 is exposed to an exterior space outside of the reservoir shell that has an ambient atmospheric pressure. Valve 25 may be coupled with lid 26 of the reservoir shell in a variety of ways including, but not limited to, using a snap fit, an adhesive bond, a weld, a threaded connection, a compression fit, a bayonet connection, a luer fitting, and the like. In some cases, a seal or a gasket, such as one or more O-rings, may be included. In some embodiments, valve 25 or portions of valve 25 may be integrally molded with portions of reservoir 14. In alternative embodiments, valve 25 may be engaged with reservoir 14 using a tube, a fitting, a coupling, and the like.

Figure 3:
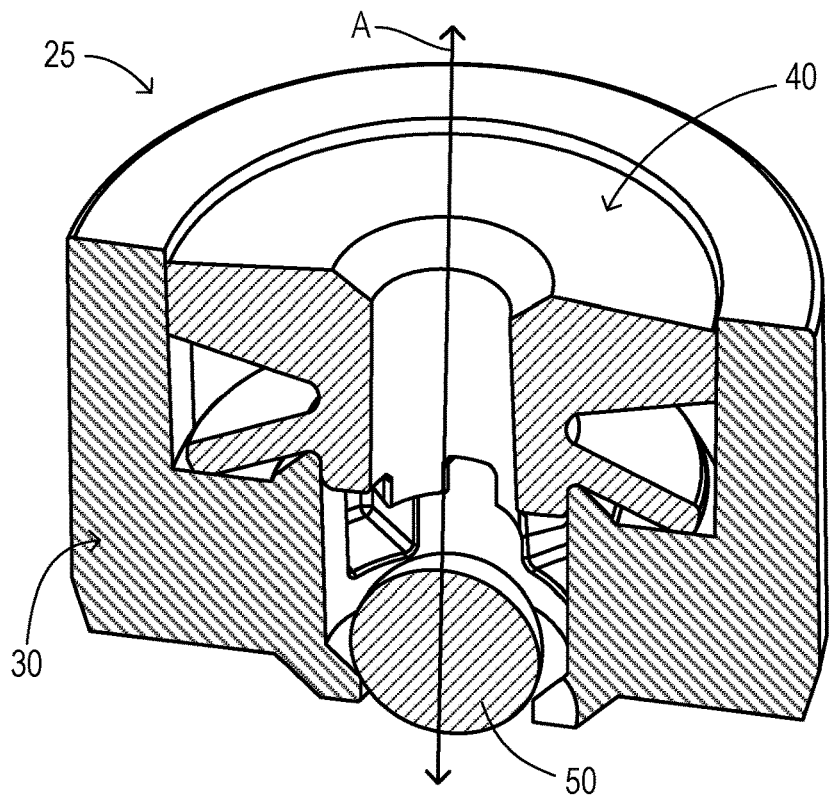
FIG. 3 is a center, vertical cross-sectional view of a relief valve according to a first embodiment.

A first embodiment of two-way pressure relief valve 25 is shown in greater detail in FIGS. 3-11. The cross section of FIG. 3 shows a main body 30, a sealing disk 40, and a sealing ball 50 of valve 25, wherein a ball valve for positive pressure relief and a diaphragm valve for negative pressure relief are both in a closed state.

A main body 30, which is adapted to mount into a wall of the reservoir, is formed of a rigid biocompatible material (e.g., a molded thermoplastic). Main body 30 is generally cup-shaped with a central chamber 31. Chamber 31 is tiered, so that a flat ledge forms an outer radial seat 32 extending annularly around a center axis A of valve 25. Preferably, outer radial seat 32 is a flat annular surface oriented perpendicular to center axis A, but can be frustoconical or other shapes that can form a controllable seal with sealing disk 40. An upper portion of chamber 31 receives sealing disk 40 and a lower portion of chamber 31 forms a positive-pressure port at center axis A with an inner radial seat 33 around a central opening that receives sealing ball 50.

Figure 4:
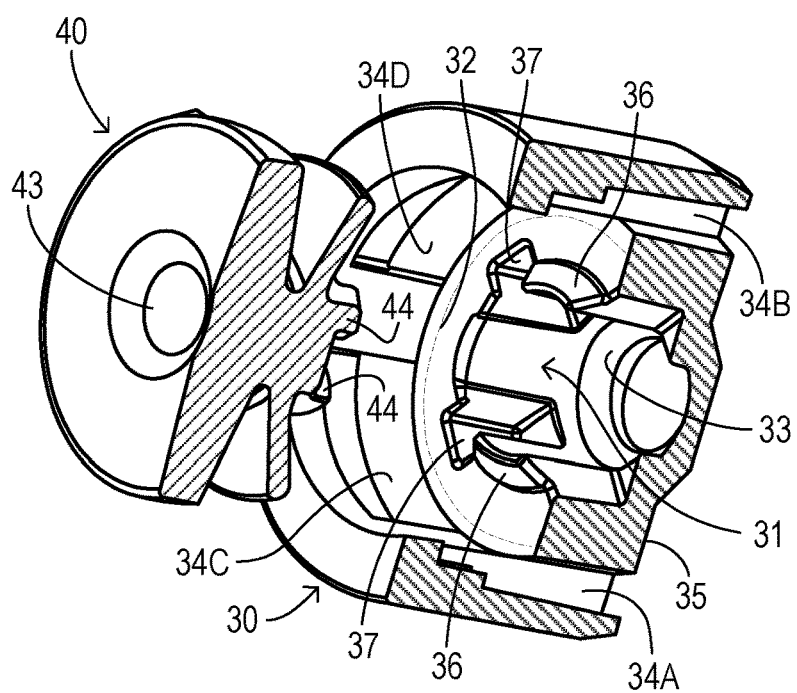
FIG. 4 is an off-center cross-sectional view of a main body and a sealing disk of the relief valve of FIG. 3.
Figure 5:
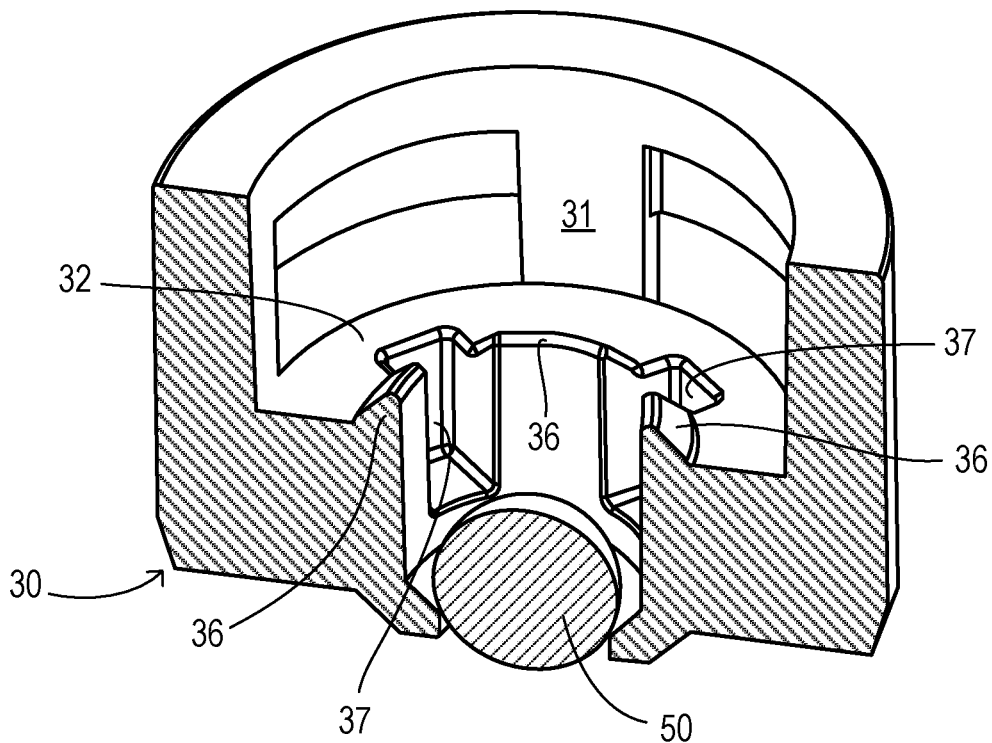
FIG. 5 a vertical cross-sectional view of the main body and a sealing ball of the relief valve of FIG. 3.
Figure 6:
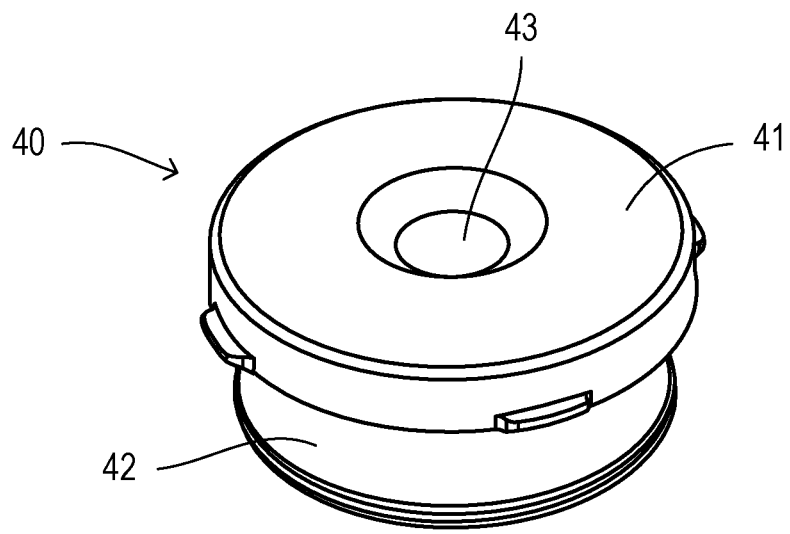
FIGS. 6 and 7 are perspective views of the sealing disk of FIG. 3.

Main body 30 has one or more internal passages spanning outer radial seat 32 in order to provide a negative-pressure port. As shown in FIG. 4, main body 30 has internal passages 34A, 34B, 34C, and 34D extending axially from a bottom surface 35 (providing the negative pressure port) to openings in an inner cylindrical surface of main body 30 above outer radial seat 32. Passages 34A, 34B, 34C, and 34D are annularly spaced around the periphery of outer radial seat 32. By spanning outer radial seat 32, the negative pressure port can be fluidically coupled to ambient external air by opening of the diaphragm valve as described below. Resulting flowpaths 60 and 61 provide negative pressure relief.

Sealing disk 40 retained in central chamber 31 comprises an anchor body 41 and a flexible diaphragm 42. Disk 40 is preferably formed as a solid block of a resilient material, such as a biocompatible silicon rubber. In cross section, anchor body 41 and diaphragm 42 have a butterfly shape, wherein diaphragm 42 is bendable toward and away from anchor body 41. Preferably, diaphragm 42 is shaped as an annular flange extending from anchor body 41 with a frustoconical shape. Anchor body 41 is fixed (e.g., glued, press-fit, or snapped) to main body 30 within the upper portion of central chamber 31 such that diaphragm 42 is biased against outer radial seat 32. Anchor body 41 defines an axial passage 43 coupling central chamber 31 to the external air at ambient pressure (e.g., atmospheric pressure outside the reservoir).

Main body 30 further defines axial wedges 36 alternating with adjacent axial grooves 37. Wedges 36 extend upward to bear against sealing disk 40 at the base of diaphragm 42. Grooves 37 between wedges 36 fluidically couple an ambient-pressure side (i.e., lower surface) of diaphragm 42 to ambient pressure via axial passage 43 of sealing disk 40. A reservoir-pressure side (i.e., upper surface) of diaphragm 42 is fluidically coupled to the interior airspace (i.e., internal pressure $P_i$) by passages 34A-34D.

Figure 7:
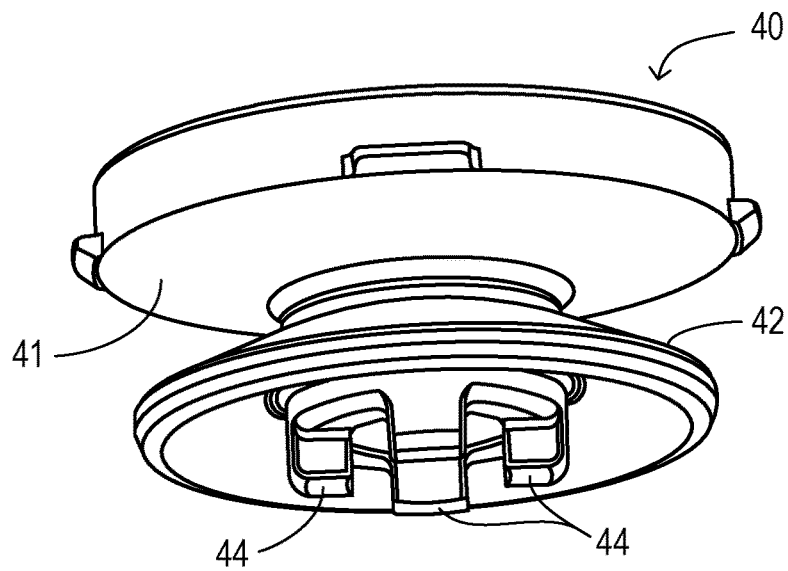
Figure 8:
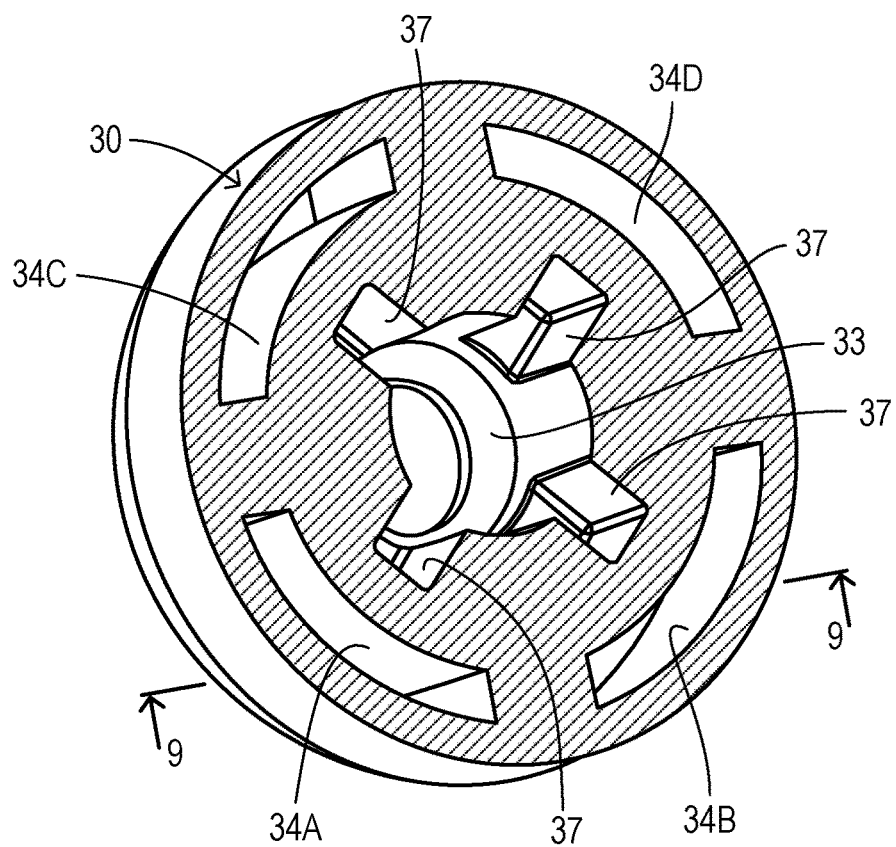
FIG. 8 is a horizontal, cross-sectional view of the main body of the relief valve of FIG. 3.
Figure 9:
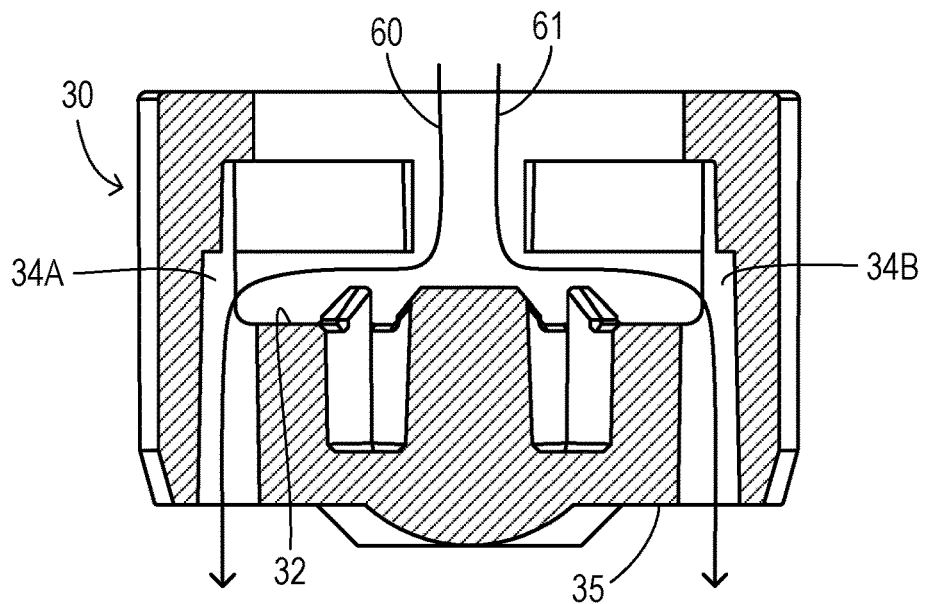
FIG. 9 is a vertical, cross-sectional view of the main body of FIG. 3 taken along line 9-9 of FIG. 8, indicating gas flowpaths for negative pressure relief.

Sealing ball 50 may be comprised of a resilient material (such as nylon). In the embodiment of FIGS. 3-11, ball 50 is biased against inner radial seat 33 by gravity (i.e., by the weight of ball 50). For achieving a good seal, inner radial seat 33 may have a frustoconical surface. As shown in FIGS. 4 and 7, sealing disk 40 preferably includes a plurality of axial protrusions 44 which are annularly spaced to receive ball 50 when it moves to an upper (full open) position. Protrusions 44 limit the lifting of sealing ball 50 to maintain open spaces between protrusions 44 which prevents blocking of axial passage 43 by ball 50. With ball 50 lifted off of inner radial seat 33, a gas flowpath for positive pressure relief is provided through the central opening of main body 30 and axial passage 43 of sealing disk 40.

Figure 10:
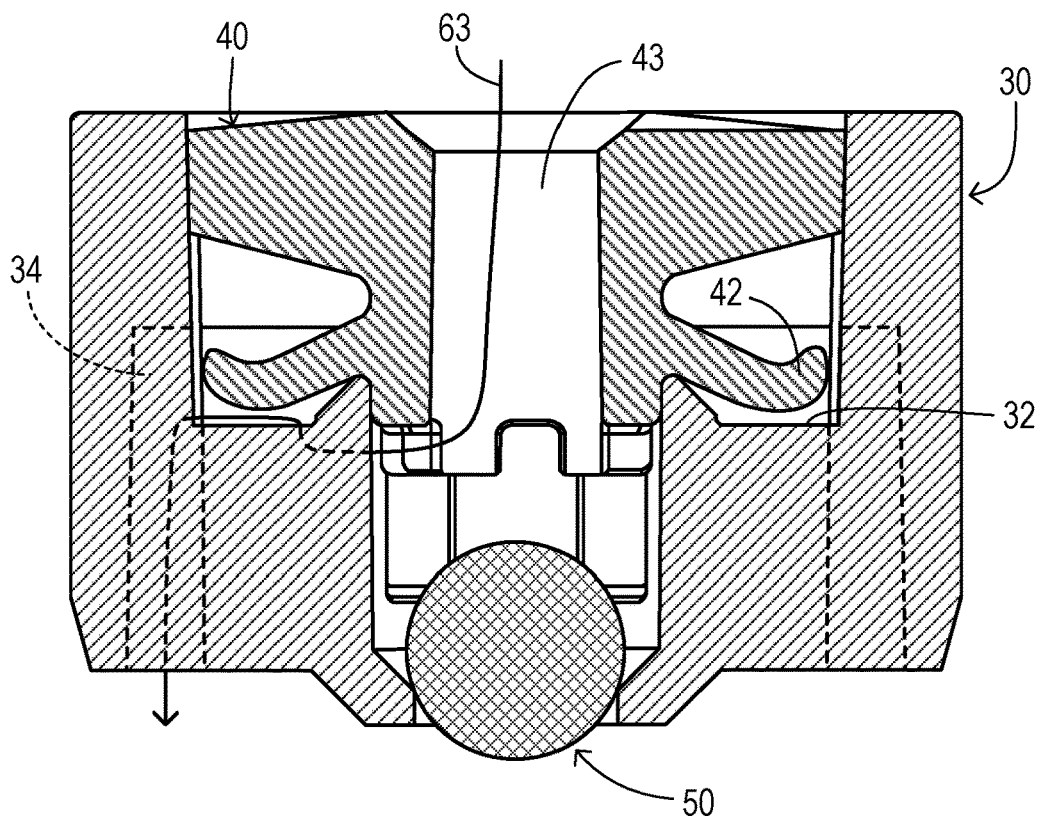
FIG. 10 is a vertical, cross-sectional view of the relief valve of FIG. 3 indicating gas flowpaths for negative pressure relief.

When a pressure differential across valve 25 is low or below selected thresholds, ball 50 and diaphragm 42 are seated against valve seats 32 and 33. As shown in FIG. 10, when the pressure inside the reservoir ($P_i$) is below the external ambient pressure ($P_e$) by a negative-pressure threshold, then diaphragm 42 is lifted off outer radial seat 32 to intake a gas from the atmosphere into the reservoir through axial passage 43, internal passages 34, and the negative-pressure port where passages 34 meet surface 35 (e.g., along flowpath 63). The negative-pressure threshold can be determined according to a shape and thickness of diaphragm 42, its constituent material properties, and an amount of bias deflection determined by its placement relative to outer radial seat 32.

Figure 11:
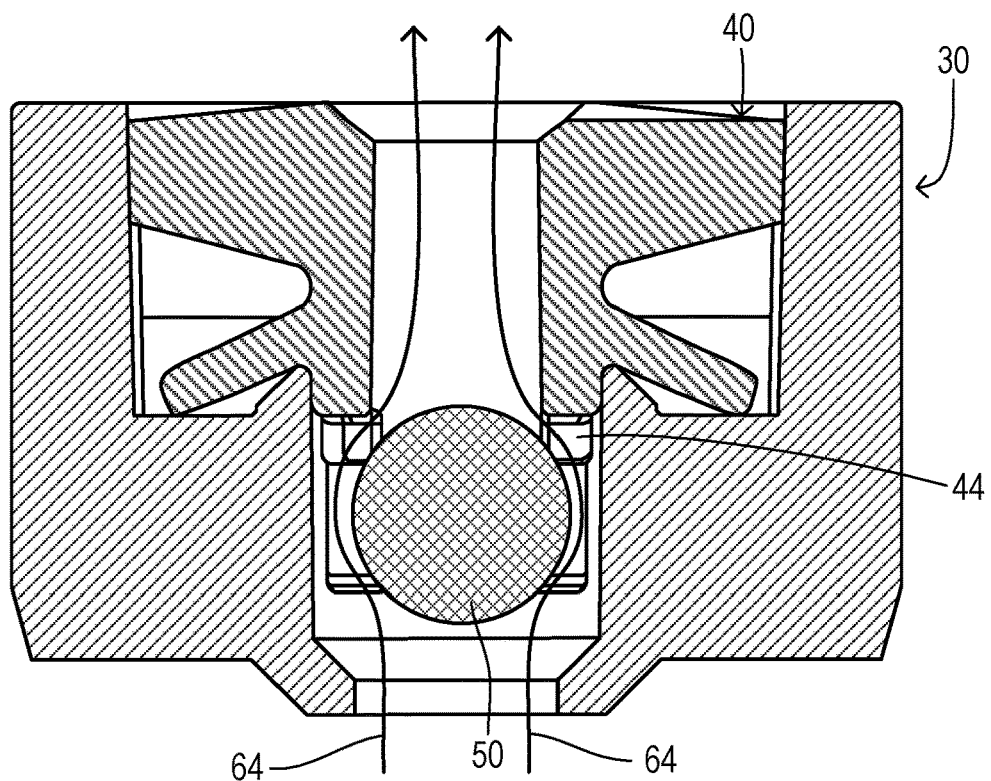
FIG. 11 is a vertical, cross-sectional view of the relief valve of FIG. 3 indicating gas flowpaths for positive pressure relief.

As shown in FIG. 11, when a pressure inside the reservoir ($P_i$) exceeds the ambient pressure by a positive-pressure threshold, then sealing ball 50 is lifted off inner radial seat 33 to exhaust a gas from the reservoir through the positive-pressure port (e.g., center hole) and axial passage 43 to the external airspace (i.e., atmosphere) along a flowpath 64. The positive-pressure threshold can be determined according to a size (e.g., weight) and constituent material properties of ball 50.

Figure 12:
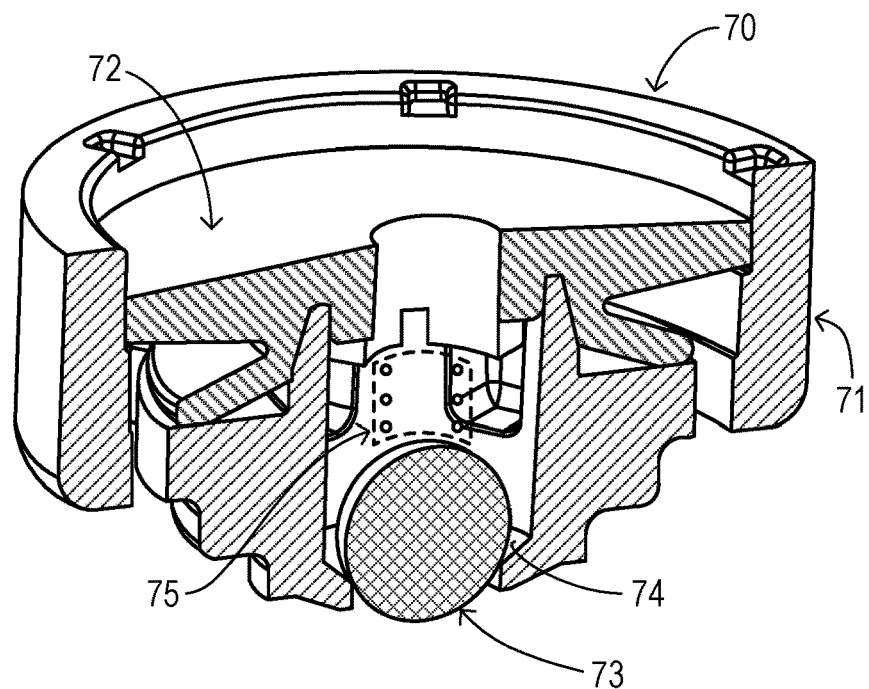
FIG. 12 is a vertical, cross-sectional view of a relief valve according to another embodiment of the invention.

FIG. 12 show an alternative embodiment of a two-way pressure relief valve 70 having slightly different dimensions, resulting in different pressure thresholds, for example. A main body 71 receives a sealing disk 72 and a sealing ball 73. In addition to the weight of ball 73 biasing is against a valve seat 74, a compressible body 75 is disposed between ball 73 and sealing disk 72. Compressible body 75 is configured to bias sealing ball 73 against valve seat 74 according to a force selected to provide the desired positive-pressure threshold. Compressible body 75 can be comprised of a toroidal spring, for example.

What is claimed is:

1. A differential pressure relief valve for a medical reservoir, comprising:
   a main body adapted to mount to a wall of the reservoir, wherein the main body has a central chamber defining an outer radial seat, wherein the main body has a positive-pressure port at a center axis with an inner radial seat, and wherein the main body has a negative-pressure port comprising an internal passage spanning the outer radial seat;
   a sealing disk having an anchor body retained in the central chamber and a flexible diaphragm biased against the outer radial seat, wherein the anchor body defines an axial passage coupling the central chamber to an ambient pressure of an atmosphere outside the reservoir; and a sealing ball biased against the inner radial seat;
wherein when a pressure inside the reservoir exceeds the ambient pressure by a positive-pressure threshold, then the sealing ball is lifted off the inner radial seat to exhaust a gas through the positive-pressure port and the axial passage to the atmosphere; and
wherein when the pressure inside the reservoir is below the ambient pressure by a negative-pressure threshold, then the diaphragm is lifted off the outer radial seat to intake a gas from the atmosphere into the reservoir through the axial passage, the internal passage, and the negative-pressure port.

2. The valve of claim 1 wherein the sealing ball is gravitationally biased against the inner radial seat.

3. The valve of claim 1 further comprising a compressible body biasing the sealing ball against the inner radial seat.

4. The valve of claim 1 wherein the inner radial seat is comprised of a frustoconical surface.

5. The valve of claim 1 wherein the sealing disk includes a plurality of axial protrusions limiting the lifting of the sealing ball to prevent blocking of the axial passage.

6. The valve of claim 1 wherein the main body comprises a plurality of internal passages spanning the outer radial seat, wherein the internal passages include axial sections providing a plurality of openings for the negative-pressure port, and wherein the axial sections are annularly spaced and each has a respective opening coupled to an internal-pressure side of the diaphragm.

7. The valve of claim 1 wherein the outer radial seat is comprised of an annular surface.

8. The valve of claim 7 wherein the annular surface extends perpendicular to the center axis.

9. The valve of claim 7 wherein the diaphragm is comprised of an annular flange extending from the anchor body.

10. The valve of claim 9 wherein the annular flange has a frustoconical shape.

11. The valve of claim 1 wherein the main body defines axial wedges alternating with adjacent axial grooves, wherein the wedges bear against the sealing disk, and wherein the grooves fluidically couple an ambient-pressure side of the diaphragm to the ambient pressure via the axial passage of the sealing disk.

12. A medical fluid reservoir system, comprising:
a reservoir shell, the reservoir shell defining an interior space inside of the reservoir shell that is configured to contain a medical fluid and an exterior space that is outside of the reservoir shell; and
a differential pressure relief valve that is coupled to the reservoir shell, the differential pressure relief valve comprising:
a main body adapted to mount to a wall of the reservoir, wherein the main body has a central chamber defining an outer radial seat, wherein the main body has a positive-pressure port at a center axis with an inner radial seat, and wherein the main body has a negative-pressure port comprising an internal passage spanning the outer radial seat;
a sealing disk having an anchor body retained in the central chamber and a flexible diaphragm biased against the outer radial seat, wherein the anchor body defines an axial passage coupling the central chamber to an ambient pressure of the exterior space; and
a sealing ball biased against the inner radial seat;
wherein when a pressure in the interior space exceeds the ambient pressure by a positive-pressure threshold, then the sealing ball is lifted off the inner radial seat to exhaust a gas through the positive-pressure port and the axial passage to the exterior space; and
wherein when the pressure in the interior space is below the ambient pressure by a negative-pressure threshold, then the diaphragm is lifted off the outer radial seat to intake a gas from the atmosphere into the interior space through the axial passage, the internal passage, and the negative-pressure port.

13. The reservoir system of claim 12 wherein the sealing ball is gravitationally biased against the inner radial seat.

14. The reservoir system of claim 12 further comprising a compressible body biasing the sealing ball against the inner radial seat.

15. The reservoir system of claim 12 wherein the sealing disk includes a plurality of axial protrusions limiting the lifting of the sealing ball to prevent blocking of the axial passage.

16. The reservoir system of claim 12 wherein the main body comprises a plurality of internal passages spanning the outer radial seat, wherein the internal passages include axial sections providing a plurality of openings for the negative-pressure port, and wherein the axial sections are annularly spaced and each has a respective opening coupled to an internal-pressure side of the diaphragm.

17. The reservoir system of claim 12 wherein the outer radial seat is comprised of an annular surface.

18. The reservoir system of claim 17 wherein the diaphragm is comprised of an annular flange extending from the anchor body.

19. The reservoir system of claim 18 wherein the annular flange has a frustoconical shape.

20. The reservoir system of claim 12 wherein the main body defines axial wedges alternating with adjacent axial grooves, wherein the wedges bear against the sealing disk, and wherein the grooves fluidically couple an ambient-pressure side of the diaphragm to the ambient pressure via the axial passage of the sealing disk.

* * * * *